United States Patent
Tulloch et al.

(10) Patent No.: US 11,534,586 B2
(45) Date of Patent: *Dec. 27, 2022

(54) LIQUID TREATMENT DISPENSER

(71) Applicant: AAN MEDICAL LIMITED, Salisbury (GB)

(72) Inventors: Andrew Tulloch, Reading (GB); Andrew Coats, Salisbury (GB); Nigel Davis, Kenilworth (GB); Thomas Drew, Salisbury (GB)

(73) Assignee: AAN MEDICAL LIMITED, Salisbury (GB)

( * ) Notice: Subject to any disclaimer, the term of this patent is extended or adjusted under 35 U.S.C. 154(b) by 780 days.

This patent is subject to a terminal disclaimer.

(21) Appl. No.: 16/476,357

(22) PCT Filed: Jan. 10, 2018

(86) PCT No.: PCT/GB2018/050055
§ 371 (c)(1),
(2) Date: Jul. 8, 2019

(87) PCT Pub. No.: WO2018/130822
PCT Pub. Date: Jul. 19, 2018

(65) Prior Publication Data
US 2020/0038642 A1 Feb. 6, 2020

(30) Foreign Application Priority Data
Jan. 13, 2017 (GB) ...................................... 1700609

(51) Int. Cl.
*A61M 35/00* (2006.01)
*G16H 40/63* (2018.01)
*G16H 20/13* (2018.01)

(52) U.S. Cl.
CPC ............ *A61M 35/20* (2019.05); *G16H 20/13* (2018.01); *G16H 40/63* (2018.01);
(Continued)

(58) Field of Classification Search
CPC .............. A61M 35/20; A61M 2205/13; A61M 2205/18; A61M 2205/3313;
(Continued)

(56) References Cited

U.S. PATENT DOCUMENTS 1,089,595 A * 3/1914 Sopha ................. A61M 35/003
604/289
10,500,026 B2 * 12/2019 Coats ................... A61M 11/006
(Continued)

FOREIGN PATENT DOCUMENTS

WO 2012/043075 4/2012
WO 2015/028787 3/2015

OTHER PUBLICATIONS

International Search Report for PCT/GB2018/050055, dated Apr. 4, 2018, 3 pages.
(Continued)

*Primary Examiner* — Garcia Ade
(74) *Attorney, Agent, or Firm* — Nixon & Vanderhye P.C.

(57) ABSTRACT

A cartridge acting as a dispenser for liquid treatments of a human or animal body is U shaped or hoop shape. The cartridge has a container containing a liquid treatment which when required to be dispensed is ejected through one or more nozzles projecting through the wall of the cartridge into the centre of the U or of the hoop. A base is provided for cartridges, the base controlling timing and quantity of treatments.

18 Claims, 10 Drawing Sheets

(52) U.S. Cl.
CPC ..... *A61M 2205/13* (2013.01); *A61M 2205/18* (2013.01); *A61M 2205/3313* (2013.01); *A61M 2205/50* (2013.01); *A61M 2205/6054* (2013.01); *A61M 2205/6072* (2013.01); *A61M 2205/8206* (2013.01)

(58) Field of Classification Search
CPC ...... A61M 2205/50; A61M 2205/6054; A61M 2205/6072; A61M 2205/8206; A61M 35/00; G16H 20/13; G16H 40/63; B05B 9/047; B05B 9/035; B05B 9/0413; B05B 9/0423; B05B 12/122; B05B 1/207
USPC .......................................................... 604/311
See application file for complete search history.

(56) References Cited

U.S. PATENT DOCUMENTS

| | | | |
|---|---|---|---|
| 2002/0011259 A1* | 1/2002 | Pociask | B08B 3/026 134/199 |
| 2016/0158465 A1* | 6/2016 | Coats | B05B 9/0861 604/289 |

OTHER PUBLICATIONS

Written Opinion of the ISA for PCT/GB2018/050055, dated Apr. 4, 2018, 6 pages.

\* cited by examiner

LIQUID TREATMENT DISPENSER

This application is the U.S. national phase of International Application No. PCT/GB2018/050055 filed 10 Jan. 2018 which designated the U.S. and claims priority to GB Patent Application No. 1700609.9 filed 13 Jan. 2017, the entire contents of each of which are hereby incorporated by reference.

TECHNICAL FIELD

This invention relates to a cartridge for dispensing liquid treatments onto human or animal body parts. It is primarily directed to applying liquid treatments to a human or animal body part for medical or veterinary purposes.

BACKGROUND ART

Provision of drugs and other medical veterinary treatments has been usually by injection, pills, and nasal sprays; more recently transdermal patches have been used to deliver a measured amount of the drug or other treatment concerned. In this specification "treatment" includes pre-treatments of persons to minimise their risk of reaction if subsequently exposed, for example, to hazardous gases.

A small number of drugs are available in spray-on formulations, but these require significant dexterity to apply and give very inconsistent doses due to variation in the accuracy of the user, the distance of the spray from the target and the number of times and force with which the nozzle is pressed.

PTL 0001: WO WO 2015/028787.
(AAN MEDICAL LIMITED) May 3, 2015 addressed the issue of ensuring the accuracy of delivery of the drug or other treatment concerned avoiding the need, in the case of transdermal treatments, to use patches ensuring that the patch continues to adhere sufficiently to enable the drug or other treatment to cross the skin barrier for a long enough time for the treatment to be effective.

However, if the device of WO2015/028787 is used for different drugs (or with different patients), there will be a need in many cases to clean the components of the device to medical standards after use and before subsequent use because of the risk of cross contamination between treatments administered on different occasions. This can be a time consuming task. Furthermore, the pressures at the nozzles of the device of WO2015/028787 may differ running the risk of uneven application on the surface of the body to be treated.

DISCLOSURE OF THE INVENTION

According to the present invention a cartridge for liquid treatments of a human or animal body comprises a cartridge shaped as a U or a hoop and having an internal container containing treatment joined to one or a plurality of nozzles projecting through the wall of the cartridge inwards from the cartridge towards the centre of the U or hoop, wherein application of pressure to the container expels liquid treatment through the one or plurality of nozzles in the cartridge.

In one embodiment of the invention the container is connected to a cam operated displacement actuator, the cam being driven by a motor in the U or hoop member.

In another embodiment the cartridge is divided internally to form the container which has a deformable wall and a chamber is around the container, the chamber is separated from the treatment by the deformable wall, and wherein deformation of the deformable wall by increasing pressure in the chamber expels liquid treatment through the one or plurality of nozzles.

In a further embodiment the chamber is separated from the container by an elasticated diaphragm and chamber is initially evacuated, the vacuum created extending the elasticated diaphragm and holding the treatment in the container under the vacuum until the vacuum is broken relaxing the elasticated diaphragm and decreasing the volume of the container to expel treatment through the one or plurality of nozzles.

In a yet further embodiment of the invention the container has a plunger and the container is connected by tubes to the one or plurality of nozzles, depression of the plunger expelling treatment from the container through the tubes to the one or plurality of nozzles, the cartridge additionally comprising an actuator connected to the plunger operation of the actuator depressing the plunger releasing treatment from the container.

In a further embodiment of the invention, the cartridge contains both a pump in addition to the container containing the treatment.

In the latter embodiment the base, additionally, may have a data connection to the cartridge.

In the latter embodiment the base, additionally, may have an electrical connection to the cartridge through which operation of the pump is controlled.

Other features of the invention are set out in the accompanying description and claims.

MODE(S) FOR CARRYING OUT THE INVENTION

Figure 1:
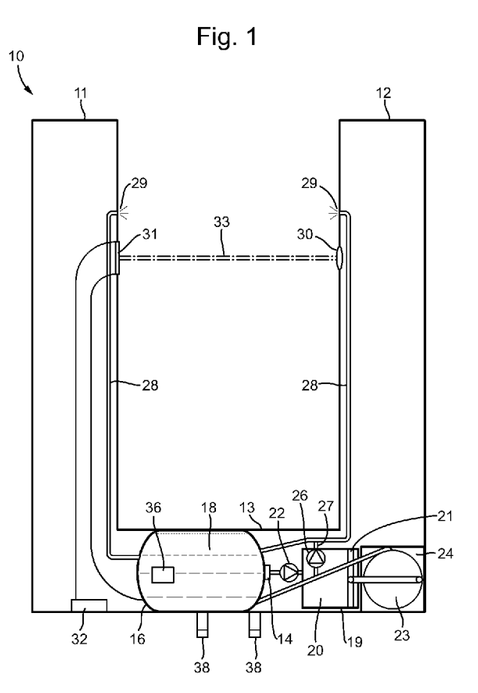
FIG. 1 shows schematically a vertical section through a first example of the invention with a U-shaped cartridge.
Figure 2:
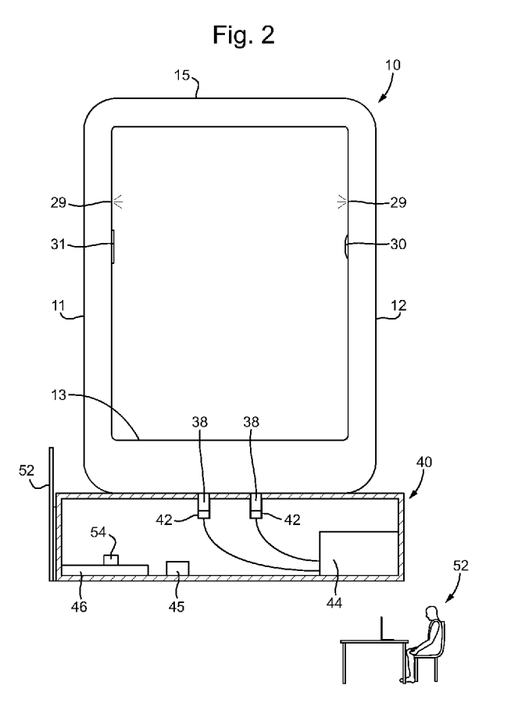
FIG. 2 shows the first example this time with a hoop cartridge mounted on a base, the base being in section.

FIGS. 1 and 2 show cartridge 10 (U-shaped in FIG. 1 and hoop shaped in FIG. 2). In FIG. 1 the cartridge is in section. In FIG. 2 the cartridge 10 is shown mounted on a base 40, which is in section.

In FIG. 1, a cartridge 10 according to the invention is U-shaped with arms 11 and 12 extending upwards from the bottom of the U 13. In FIG. 2 arms 11 and 12 are sides of a substantially rectangular hoop, the arms 11 and 12 being joined bottom 13 and top 15; as shown the hoop has its sides 11 and 12 longer than the bottom and top 13, 15, but it has been found that some users prefer a hoop structure in which the bottom and top 13 and 15 are longer than the sides 11 and 12.

Returning to FIG. 1, a container clip 14 is provided in the bottom 13 of the U in which a container 16 containing liquid treatment 18 is mounted. The container 16 may be a bottle, but preferably is a deformable bag as shown. The container is connected to a displacement actuator 19. The actuator 19 has a chamber 20 with a piston 21 operating to and fro within the chamber 20. There is one way valve 22 between the container 16 and chamber 20. The piston 21 is connected to a cam 23 operated by a micro motor 24. A half turn of the motor drives the piston to draw liquid treatment 18 from the container 16 through the one way valve 22 into the chamber 20. A further half turn of the motor, drives the treatment from the chamber 20 through a further one way valve 26 and connector 27 into a pair of tubes 28, one of the pair passing through one arm 11 of the cartridge 10 the other through the other arm 12 each to nozzles 29 directed inwards from the arms 11 and 12.

Infrared lamp 30 and receiver 31 are mounted on the arms 12 and 11 opposite one another to detect the presence of a body part between them. The receiver 31 connects to a switch 32 which controls power to the motor 24, the motor being switched on when the IR beam 33 is broken and thus the receiver 31 detects the presence of a body part between the arms 11 and 12.

The container 16 optionally may have a NFC or RFID chip 36 attached. The chip could contain information about the content of the container, the required usage, date of manufacture, serial number and/or expiry date for example.

The cartridge 10 is supplied to a patient as a sealed disposable unit which connects to a base, identical to item 40 shown in FIG. 2.

FIG. 2 shows a variant of the geometry of the cartridge, here the cartridge is a closed generally rectangular hoop rather than a U-shape open at the top. The bottom 13 of the hoop contains exactly the same items as described in FIG. 1 with liquid connections for treatment to flow to the nozzles 29. The cartridge 10 is shown in FIG. 2 connected to a base 40.

The base 40 has a socket 42 to receive pins of a plug 38 at the base of the cartridge 10. The socket 42 is connected to a mains transformer 44 which provides power through the plug and socket 38/42 to the infra-red lamp 30 and detector 31 and the motor switch 32 (see FIG. 1). It also powers a date chip 45 and microprocessor 46.

Experience has shown that power is best supplied though a mains connection to the transformer 44. However it is feasible to replace the mains connection and transformer with a battery. Such a battery can provide power through the plug and socket 38/42 to the motor switch 32 and infra-red lamp 30 and detector 31. The motor switch 32 (FIG. 1) and the infra-red lamp 30 and detector 31 could be powered by a separated battery mounted in the cartridge, but this may lead to complications in disposal of cartridges after use and is less reliable.

With power provided through the base 40, when the cartridge 10 is mounted in base 40 and the detector combination 31 detects that a body part is place between the arms 11/12 of cartridge 10, the switch 32 powers the motor 24 driving the cam 23 to operate piston 21, by turns drawing liquid treatment 25 from container 18 into chamber 20 and then expelling it, through valve 26 into tubes 11 and 12 and thus through nozzles 29, so spraying the treatment 25 onto the body part concerned (see FIG. 1).

By monitoring the power supply through plug and socket 38/42, the microprocessor 46 can monitor the number of times the motor 24 is operated and the period of operation. This information can be merged with the date chip to provide also information on the date and time of operation. Combining that with information received from the NFC/RFID chip 36 on the container 18, the microprocessor can calculate the volume of treatment left in the container, compliance by the patient with the dosing regimes, and to display the information on a display 52, to operate an alarm when a treatment is due, or transmit the information through a further NFC or RFID chip 54 to a remote monitoring station 56 which can check on the patient and his/her needs re-supplying treatments as needed. The microprocessor 46 can also prevent power reaching the motor 24 if a treatment is requested too soon after a previous treatment.

As an alternative to or in addition to an NFC/RFID chip on container 16, the base 40 may have a scanner or bar code reader which reads a bar code label or chip attached to the cartridge 10: the bar code containing information to identify the date of manufacture of the treatment, the nature of the treatment and dosage quantities and frequencies. A similar system is described below in relation to FIGS. 6 to 8.

Furthermore means can be provided in the system whereby the patient identifies themselves; for example this can be by insertion by the patient of a code, or by the patient wearing a tag or communication device which must be recognised by the microprocessor.

As noted previously, it is preferred that the container 16, in the embodiment of FIGS. 1 and 2 is a deformable bag. If the container 16 is not deformable, an air supply will be needed to the container, to replace liquid in the container which has been expelled, otherwise low pressure in the container will prevent satisfactory operation.

The device as described in FIGS. 1 and 2 has the advantage over the device of WO2015/028787 for medical use, in that the base 40 does not come into contact with the liquid treatment 24 and does not require cleaning to medical standards. The cartridge 10 is disposable; but could be returned to a pharmacist for cleaning and reuse if that is preferred.

The nozzles 29 can be set up to remain closed until the pressure in the hoop has reached the desired operating pressure to prevent premature operation of the spray.

Figure 3:
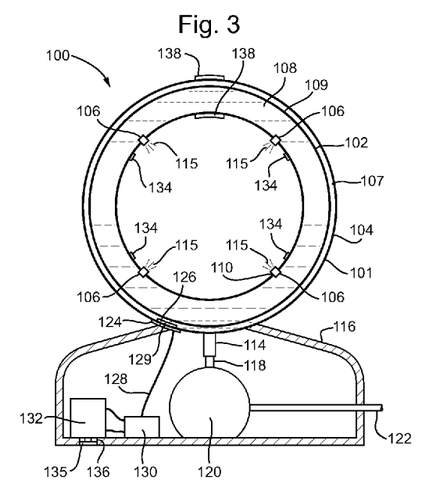
FIG. 3 is a side view in partial section of a second example of the invention.
Figure 4A:
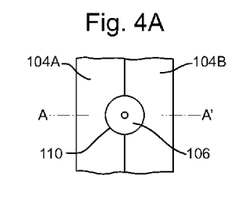
FIG. 4A is a detail view of a nozzle of FIG. 3 seen from inside the hoop.
Figure 4B:
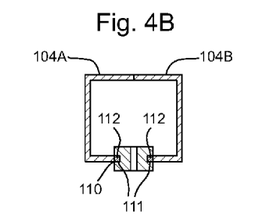
FIG. 4B is a cross section of the nozzle and hoop on the line A-A' of FIG. 4A.

In FIGS. 3 and 4, a dispenser 100 comprises a cartridge 101 having a circumferential disposable deformable bag 102 mounted in a hoop 104. The wall of the bag divides the cartridge 101 into a container109 containing a liquid treatment 108 and a chamber107 around the container 109. The bag, when mounted in the hoop, has one or more nozzles 106 directed inwardly towards the centre of the hoop. The hoop is divided vertically into two halves 104A and 104B vertically, the two halves being clipped together top and bottom of the hoop using clips 138.

The hoop 104 has one or more apertures 110 in which the nozzles 106 are mounted. The outside surface of the nozzles 106 have a waist 111 holding a seal 112 held to form a gas tight joint against the inner perimeter of the apertures 110.

The hoop has a connector 114 to the chamber 107 which, when the hoop is mounted in stand 116, forms an air tight joint onto the outlet 118 of a pump 120. In operation, the pump 120 draws air in from the surrounding atmosphere through an inlet duct 122, and pumps it under pressure into the chamber 107 around the deformable bag 102. The pressurised air surrounding the bag 102 deforms it, forcing some or all of the liquid treatment 108 to be expelled as a spray 115 though the nozzle(s) 104.

The hoop has a scanner or bar code reader 124 which reads a bar code label or chip 126 attached to the cartridge 101. The latter contains information about the content of the cartridge 101. This information is fed by a multiplex link 128 to a programmable chip 130, connected to the hoop by a connection 129.

The pump 120 is powered from a battery or mains source 132. In most cases the pump 120 would be triggered by one or more sensors 134 co-operating with the programmable chip mounted on the hoop 102 and facing inwards to identify the presence of, orientation and form of a body part placed within the hoop 102. The sensors are connected though wire links (not shown for clarity) to the connector 129 and thus to multiplex link 128. A switch 135 operated through an aperture 136 in the base of the stand 116 can be used to turn the pump on and off pressurising the hoop 104. However, the switch 135 in some arrangements may more conveniently be placed on the side of the base or isolated from user intervention altogether within the case.

The programmable chip 130 is set up to reflect the specific needs and doses required to be given to person or animal. In particular the programmable chip 130 can be set to limit the length of time during which the pump is switched on and/or to prevent operation of the pump 120 for a pre-set period following its previous operation. The programmable chip may also be programmed to vary the pressure delivered by the pump and thus the density and spread of any spray ejected through the apertures 106.

As a further development, the programmable chip 130 is linked to the internet to inform a chemist or carer etc., that a bag has been loaded and the nature of its content. It can also be used to inform doctors, nurses, or carers of the time that the device was operated and the duration of the operation. Furthermore, it could be used to activate an alarm if a treatment was not administered at the right time.

In a further refinement, a chip or reader, facing inward from the hoop reads a bar code or radio frequency identification (RFID) tag on a patient or animal as a means of primary identification that the anticipated person or animal is inserting a body part into the hoop for treatment. If the correct code or tag is not identified, the programmable chip will not allow the pump to operate.

After treatment (or when exhausted), the hoop 104 is removed from the stand 116 and the bag 102 is removed from the hoop 104, by opening clips 108 to separate the two halves 104A and 104B of the hoop. The bag 102 is then replaced, with the nozzles 106 of the new bag being located in the apertures 110 of the hoop 102. In this arrangement the bag containing medicament forms a disposable cartridge.

The device as described in FIGS. 3 and 4 has the advantage over the device of WO2015/028787 for medical use, in that the stand 116, pump 130, and other components mounted in the stand 116 do not come into contact with the liquid treatment 108 and do not require cleaning to medical standards, the bag is disposable and only the hoop 104 needs to be cleaned to medical standards if it is reused.

This elimination of cleaning can be taken one step further, by gluing the two halves of the hoop 104A and 104B together and eliminating clips 108, making the hoop 104 containing the bag 102 itself the disposable after use.

The nozzles 106 can be set up to remain closed until the pressure in the hoop has reached the desired operating pressure to prevent premature operation of the spray.

Figure 5:
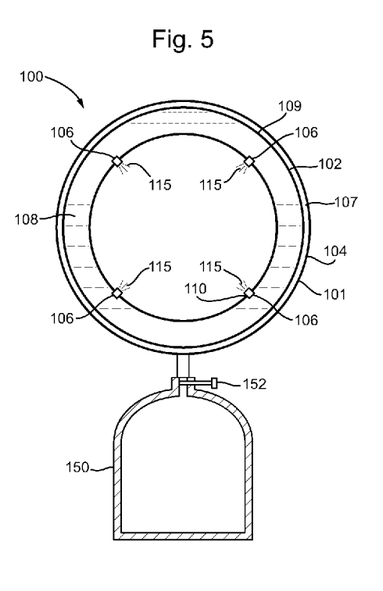
FIG. 5 is a side view in partial section of a different arrangement of the second example of the invention.

In FIG. 5, the dispenser 100 comprises a cartridge 101 as shown in FIG. 3 but with the parts of the hoop 104 glued together. The clip (138 in FIG. 3) is thus eliminated. In this example too, the sensors (134 in FIG. 3) are omitted.

Rather than being mounted on a base (116 in FIG. 3) the cartridge 101 is mounted on a gas container 150. Normally the gas cylinder or cartridge contains compressed air, but other suitable compressed gases could be used. The gas container 150 has a control valve 152, this is shown as hand operated, but in other arrangements, the gas container 150 could be a single discharge device discharging the correct volume of gas into the chamber 107 for a single operation of the dispenser, after which the cartridge including gas container 150 is thrown away.

It can be seen that the embodiment of FIG. 5 avoids the need to clean any apparatus to medical standards after use.

Figure 6:
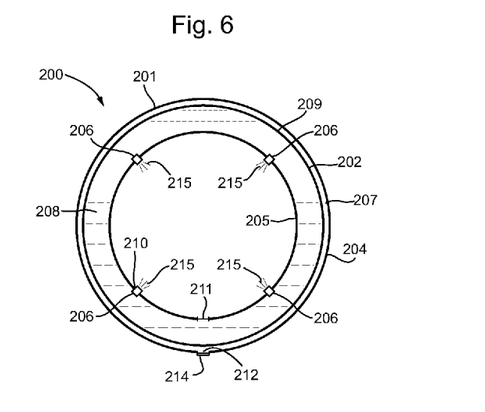
FIG. 6 is a side view of a third example of the invention.

Another example of the invention is shown in FIG. 6. Here a dispenser 200 is formed of a cartridge 201 comprising a hoop 204 divided internally by a deformable elasticated diaphragm 202. The cartridge is operated manually. It is a very simple device, operated manually by breaking a seal 214.

The hoop 204 and a diaphragm 202 are supplied as a sealed cartridge 201. The diaphragm 202 divides the cartridge into two; a container 209 containing the liquid treatment 208 and an outer chamber 207. The hoop has a flat inner wall 205 in which nozzles 206 are mounted having air tight seals within apertures 210 in the hoop 204. The diaphragm 202 is made of an elasticated material, such as medical grade silicon rubber, and is mounted in the hoop so that in its upstretched configuration it stretches across the inside of inner wall 205. The hoop 204 is air tight and chamber 207 is evacuated of air through duct 212 on assembly so that the diaphragm 202 stretches. The duct 212 is then sealed with a seal 214. As the evacuation occurs, the required treatment 208 is admitted into the container 209 between the expanded diaphragm 202 and the inside of the inner wall 205 of the hoop through an aperture 211 in the inner wall 205; the aperture 211 is then permanently sealed off. The liquid treatment 208 is thus held in place between the diaphragm and the inside of inner wall 205 under the influence of the vacuum formed in the chamber 207 after evacuation of air acting on diaphragm 202.

The cartridge 201 is placed around a body part to be treated and the seal 214 broken admitting air into the chamber 207. The vacuum holding the diaphragm 202 in its stretched state is thus lost and diaphragm 202 relaxes to its unstretched position, forcing the treatment 208 out through nozzles 206 as a spray 215 onto any body part inserted in the hoop 204. After treatment, the cartridge 201 and content is disposed of.

The nozzles 206 close when the pressure in the container 209 drops below a predetermined level, to prevent any residual treatment dribbling out of the cartridge 201.

It is likely, in practice, that the simple device of FIG. 6 would not be used by a medical professional on many occasions when spraying medical treatments where close control of the treatment regime is needed. Nonetheless the device of FIG. 6 is very suitable for non-professional use when the medical treatment regime is not sensitive or the treatment is of a veterinary such as sun blocking or tanning lotion. This embodiment is disposed of after use and thus requires no cleaning to medical standards.

Figure 7:
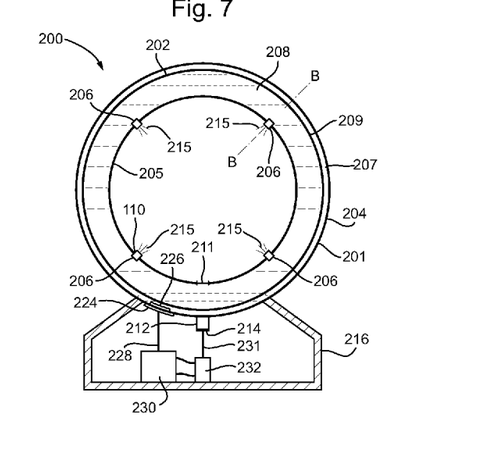
FIG. 7 is a side view in partial section of another arrangement of the example of the invention.
Figure 8A:
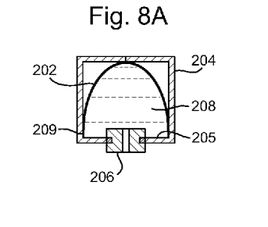
FIG. 8A is a section on the line B-B' of FIG. 7 prior to release of a treatment.
Figure 8B:
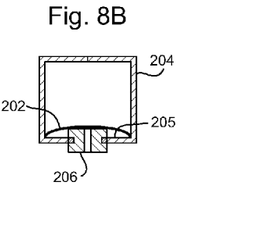
FIG. 8B is a section on the line B-B' of FIG. 7 after release of a treatment.

The embodiment in FIG. 6 is developed further in FIGS. 7 and 8.

In FIGS. 7 and 8, the cartridge 201 is mounted on a base 216.

The base 216 has a scanner or bar code reader 224 which reads a bar code label or chip 226 attached to the cartridge 201. The bar code label contains information about the content of the cartridge 201. This information is fed by a multiplex link 228 to a programmable chip 230, where the information can be stored. But as a further development, the programmable chip 230 has an internet connection which can be used to inform a chemist or carer etc., that a cartridge 201 has been loaded and the nature of its content. It can also be used to inform doctors, nurses, or carers of the time that the device was operated. However, in this arrangement the duration of the operation is fixed and is set by the specific design and content of the cartridge 201. Furthermore, the programmable chip could be used to activate an alarm if a treatment was not administered at the right time.

The base has a servo operated pin 231 to break the seal 214, the servo mechanism 232 controlling the pin 231 being controlled by the programmable chip 230 to break the seal 214 when sensors 234 disposed around the inside of the hoop 204 detect the presence of a body part to be treated within the hoop. Typically the sensors 234 are chips or reader facing inward from the hoop to read a bar code or radio frequency identification (RFID) tag on a patient or animal as a means of primary identification that the anticipated person or animal has inserted the correct body part into the hoop for treatment and it is in the right position. This information is fed to the programmable chip 230; only if the correct code or tag is identified will the programmable chip allow the pin 231 to move to break the seal 214.

A body part to be treated is placed within the hoop 204. The vacuum in chamber 207 holding the diaphragm 202 in its stretched state is broken by breaking seal 214, the diaphragm then relaxes (as in FIG. 8B) forcing the treatment out through nozzles 206 as a spray 215 onto the body part to be treated. After treatment, the cartridge 201 and content is removed from the base 216 and disposed of. The nozzles 206 close when the pressure in the container 209 drops below a predetermined level, to prevent any residual treatment dribbling out of the cartridge 201.

Figure 9:
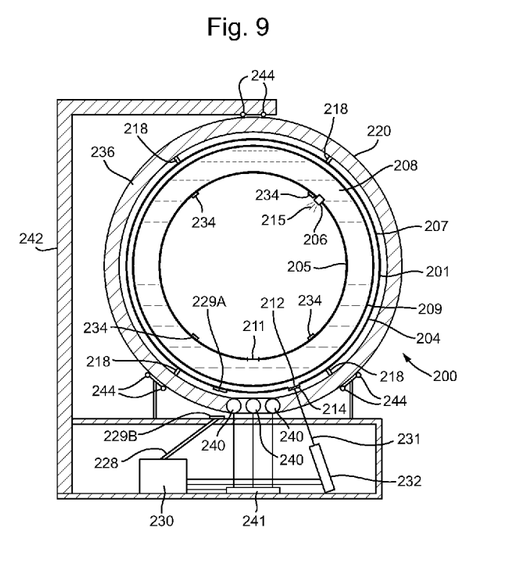
FIG. 9 is a side view in partial section of a further arrangement of the third example of the invention.

FIG. 9 shows a further development of the arrangements of FIGS. 7 and 8. Here, the dispenser 200 comprises a cartridge 201 as described in FIGS. 6 and 7; the cartridge, however, has only one nozzle 206.

The cartridge 201 is mounted using clips 218 within a circular electrically conducting disc 236, for example an aluminium disc. The disc 236 is mounted vertically in a frame 242, supported top and bottom on rollers 244. At the base of the frame either side of the disc 236 are electro-magnets 240. Supply of current from a power pack 241 to the electro magnets 240 induces eddy currents in the disc 236 causing it to rotate, in a way similar to the rotating disc of an electricity meter. The disc 236 and elector-magnets in combination form an induction motor 238 to rotate the cartridge 201. The frame 242 is mounted on a base 216 which has a programmable chip 230 with internet connections as discussed in with respect to FIG. 5.

The base 216 has a servo operated pin 231 to break the seal 214, the servo mechanism 232 controlling the pin 231 being controlled by the programmable chip 230 to break the seal when sensors 234 disposed around the inside of the hoop 204 detect the presence of a body part to be treated within the hoop. Typically the sensors 234 are chips or readers facing inward from the hoop to read a bar code or radio frequency identification (RFID) tag on a patient or animal as a means of primary identification that the anticipated person or animal has inserted the correct body part into the hoop for treatment and it is in the right position. The sensors 234 are linked to the programmable chip 230 by a transmitter and receiver 229A and 229B mounted on the cartridge 204 and stand 216 respectively and by multiplex cable 228. The programmable chip also controls the power supply from power pack 241 to the electro-magnets 240, power not being supplied to the electro-magnets 240 and the induction motor 238 not operated until the sensors 234 detect the presence of the appropriate body part.

The cartridge 201 is placed around a body part to be treated and the seal 214 broken by pin 231. The vacuum in chamber 207 holding the diaphragm 202 in its stretched state is lost and diaphragm 202 relaxes, forcing the treatment 208 out through the single nozzle 206 as a spray 215 onto the body part to be treated as the cartridge 201 rotates with disc 236. The nozzle 206 closes when the pressure in the container 209 drops below a predetermined level, to prevent any residual treatment dribbling out of the cartridge 201.

After treatment, the clips 218 holding cartridge 201 are opened and the cartridge 201 removed and disposed of.

In the examples of FIGS. 6 to 9, the cartridge 201 and contents can only be used once and the container therein contains substantially the exact liquid treatment required. All these examples avoid the need to clean any supporting apparatus, such as a stand or pump to medical standards as no other such equipment comes into contact with the treatment.

Figure 10:
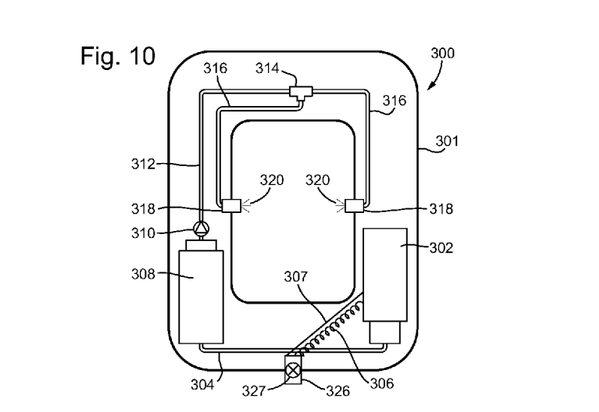
FIG. 10 is a schematic cross section of a fourth example of the invention in which a pump and treatment container are both mounted in a disposable cartridge.
Figure 11:
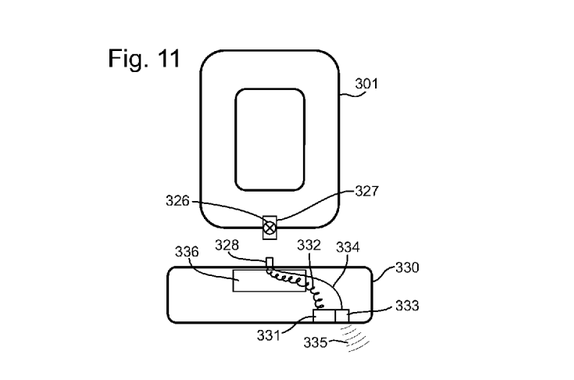
FIG. 11 shows the cartridge of FIG. 10 interacting with a base station.

FIGS. 10 and 11 show a further example of the invention being a development of the concepts in FIGS. 7 and 8, but simplified to reduce production costs and making the dispenser easier to use. A dispenser 300 comprises a hoop shaped cartridge 301 having an opposed pair of nozzles 318.

Within the cartridge an electronic pump 302 and fluid container 308, containing a treatment. The pump is connected electrically 306 to a power source though and electric/data connector 326 in the lower leg of the cartridge 301. Powering the pump drives air through silicon connecting pipe 304 into the fluid container 308, expelling treatment from the fluid container 308 into silicon connecting pipe 312 though a one way valve 310 which prevents reverse flow of the treatment. The connecting pipe 312 leads to a manifold 314 splitting the fluid flow into two along silicon connecting pipes 316 to nozzles 318. From the nozzles the treatment is expelled as a spray towards the centre of the cartridge 301 and onto any body part instead into the centre of the cartridge. Normally the design of pipes 312 and 316 is such that the distance travelled by treatment from the container 308 to the both nozzles is roughly equal to avoid any pressure differences between the sprays emanating from the nozzles.

A base station 330 is provides having an upstanding plug 328 onto which the electric/data connector 326 locates to hold the cartridge 301 in place. A valve 327 seals the cartridge 301 when the cartridge 301 is not connected to the base station, so that the inside of the cartridge is never open to the environment.

The plug 328 provides power to the cartridge from a mains transformer 331 though a connection 332; it also provides a data link to and from the pump from a programmable chip 333 through data connection 334.

The programmable chip 333 also may have NFD capability so that it can be monitored and controlled remotely if desired.

The programmable chip can also control the times at which the transformer 322 can be on, and thus availability of power to the pump 302; in addition or alternatively it can prevent power being supplied to the pump for a pre-set period after previous usage of the cartridge.

Operation of the dispenser in FIGS. 10 and 11 is simplified as no sensors are incorporated in the cartridge itself; rather the base station has one or more infra-red sensors broken by hand to turn on the electricity supply from the transformer. This can be done through the programmable chip 333 or by direct switching on of the transformer 331.

Operation pf the pump and thus consumption of treatment is monitored though the data link 307 between the pump 302 and the connecor 326 through plug 328 and data connection 334. Monitoring of usage will alert staff to the need to replace the cartridge 301 or when the dispenser is being used otherwise than in accordance with instruction or a prescription.

More sophisticated controls can be employed in the embodiment of FIGS. 10 and 11, including sensors in the inward facing walls of the cartridge as shown in FIGS. 1 and 2. Instead of a hoop, the cartridge 301 of FIGS. 10 and 11 could be U-shaped as shown in FIG. 1. Instead of the pump 302 pumping air into the fluid container 308, it could be arranged in the pipe 312 to pump treatment from the fluid container 308.

Actuation of the dispenser 300 shown in FIGS. 10 and 11 is by triggering infra-red sensors in the base; other means can be substituted, such as finger or palm print recognition, or voice recognition, or PIN actuation: however these would tend to increase price and may not be so easy to use by vulnerable patients. Similarly a system of cartridge recognition may be incorporated in the base as previously described so that the pump can only receive power if the cartridge contains a treatment which is expected—preventing cartridges containing other that prescribed treatments being operable.

In the examples of FIGS. 6 to 11, the cartridges 201/301 and contents can only be used once and the container therein contains substantially the exact liquid treatment required. All these examples avoid the need to clean any supporting apparatus, such as a stand or pump to medical standards as no other such equipment comes into contact with the treatment.

Figure 12:
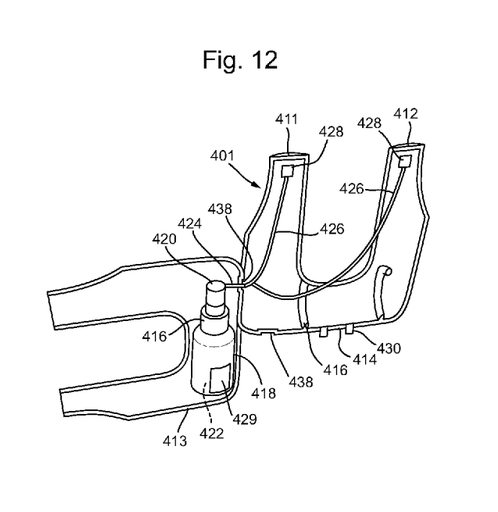
FIG. 12 shows a fifth example of the invention with a U-shaped cartridge which can be opened vertically, and shown open to show individual components.
Figure 13:
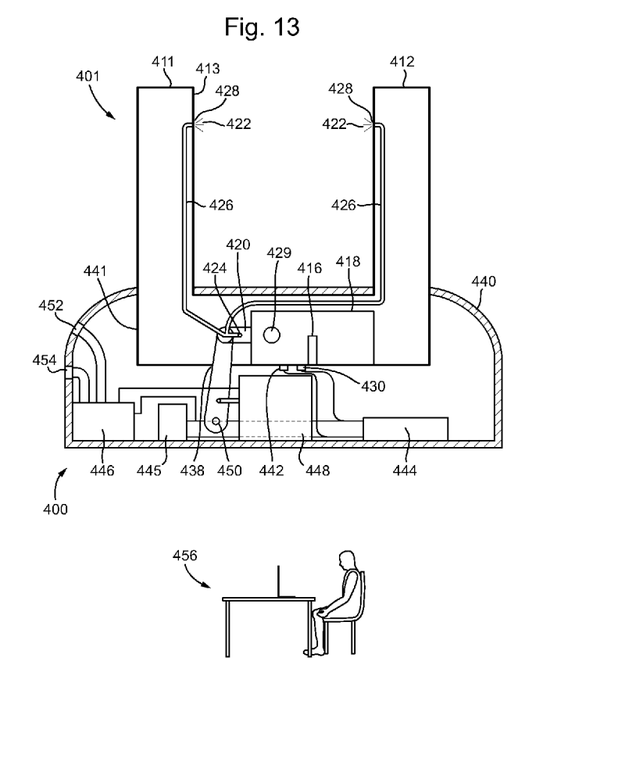
FIG. 13 a schematic vertical section though the cartridge of FIG. 12 when closed and mounted in a base.

A further example of the invention is shown in FIGS. 12 and 13 which avoids the need to dispose of the cartridge and associated items after use, and therefore, possibly is a lower cost option.

FIGS. 12 and 13 show s dispenser 400 according to the invention with a cartridge 401 which in FIG. 13 is mounted in a base 340.

The cartridge 401 is U shaped with arms 411 and 412, and is split vertically into two halves 413 and 414. In one half 413, a container 418 containing treatment 422 is mounted in a moulding 416. The container 418 has a plunger 420 depression of which forces treatment 422 from the container 418. The outlet 424 of the plunger 420 is connected to a pair of tubes 426, one passing through one arm 411 of the cartridge the other through the other arm 412 each to nozzles 428 directed inwards from the arms 411 and 412.

The container 418 optionally may have a NFC or RFID chip 419336 attached. The chip could contain information about the content of the container, the required usage, date of manufacture, serial number and/or expiry date for example.

The cartridge 401 is supplied to a patient as a sealed unit, screws 429, or as an alternative clips, hold the cartridge together, so that it can be used as a returnable unit, refilled and cleaned by a pharmacist or supplier.

The base 440 has a depression 441 in its upper surface matching the outer shape of the cartridge 401 where the cartridge is mounted in the base. A socket 442 is provided in the depression 441 to receive and connect with a plug 430 on the bottom of the U of the cartridge 401, the plug and socket being to support the cartridge 401 in place in the base 440. If desired infra-red lamp and detector can be provided to sense the presence of a body part between the arms 411 and 412 of the U as shown in FIG. 1, and if so the plug and socket can provide power from a rechargeable or replaceable battery (which can be rechargeable or replaceable) 444 in the base 440. The battery 444 also powers a date chip 445 and microprocessor 446 and actuator 448. The actuator 448 has an arm 450 extending from the surface of the base in the depression through a slot 438 in the cartridge to engage against the plunger cap 420 of container 418.

As an alternative to the infra-red lamp and detector, an infra-detector may be placed on the base unit and operated by hand as described with reference to FIG. 11. Other methods of triggering operation of the device will be clear to the shilled designer.

However operation is triggered, the microprocessor 446 allows the battery 444 to power the actuator 448 whose arm 450 presses the plunger cap 420 releasing treatment 422 from the container 418 to the nozzles 4328 through tubes 4326, so spraying the treatment 422 onto the body part concerned.

The microprocessor 446 can monitor the number of times the actuator is operated and the period of operation, and thus combining that with information received from the NFC/RFID chip 436 on the container 418, can calculate the volume of treatment left in the container, compliance by the patient with the dosing regimes, and to display the information on a display 452, to operate an alarm when a treatment is due, or transmit the information through a further NFC or RFID chip 454 to a remote monitoring station 456 which can check on the patient and his/her needs resupplying treatments as needed. The microprocessor 446 in combination with the time chip 445 can also prevent operation of the actuator 448, if a treatment is requested too soon after a previous treatment. Furthermore means can be provided in the system whereby the patient identifies themselves; for example this can be by insertion by the patient of a code, or by the patient wearing a tag or communication device which must be recognised by the microprocessor.

Other arrangements can be derived for controlling the operation of the arm 450. In particular, it is possible to use a servo motor in the cartridge to drive a small pump to pump liquid from a container of liquid in the cartridge, to pump treatment into the tubes 426 (as seen in FIGS. 10 and 11). To ensure even spray from each nozzle 428, an individual servo motor can be associated with each individual tube 426.

In the example of FIGS. 12 and 13, the battery 444 can be replaced with a transformer; likewise where a transformer is described in the other examples, it can be replace by a batter (rechargeable or one use)

In each of the examples above provided with a programmable chip, the chip can be programme not to operate unless a pre-set time has passed since a previous treatment to prevent over frequent application of treatments.

The forgoing examples show a number of ways in which the invention may be implemented, it is emphasised that the invention is not limited to the particular examples given

The invention claimed is:

1. A cartridge for liquid treatment of a human or animal body comprising a cartridge which is shaped as a U or a hoop and having an internal container containing liquid treatment joined to one or a plurality of nozzles projecting through the wall of the cartridge inwards from the cartridge towards the centre of the U or hoop, having means to apply increased or reduced pressure to the container, said increased or decreased pressure expelling liquid treatment through the one or a plurality of nozzles.

2. The cartridge of claim 1 wherein the means to apply increased or reduced pressure comprises a displacement actuator to draw treatment form the container under reduced pressure and to discharge it to one or a plurality of fluid connections to the nozzle(s).

3. The cartridge of claim 2 wherein the cartridge additionally comprises a motor to operate a cam connected to the displacement actuator.

4. The cartridge of claim 2 wherein the displacement actuator comprises a chamber, in which a piston operates, connected to draw liquid from the container and to discharge it from the container to the nozzles under application of pressure.

5. The cartridge of claim 1 wherein the means to apply increased or reduced pressure comprises a pump pumping air into the container and in which air pumped into the container forces treatment from the container to the nozzle(s).

6. The cartridge of claim 1 wherein the cartridge is divided internally to form the container which has a deformable wall and a chamber is around the container, the chamber is separated from the treatment by the deformable wall, and wherein the means to apply increased or reduced pressure comprises deformation of the deformable wall by increasing the pressure in the chamber to expel liquid treatment through the one or a plurality of nozzles(s).

7. The cartridge of claim 1 in which the container is a deformable bag.

8. The cartridge of claim 6 in which the deformable wall is an elasticated diaphragm and the chamber is initially evacuated, the vacuum created extending the elasticated diaphragm and holding the treatment in the container under the vacuum until the vacuum is broken relaxing the elasticated diaphragm and decreasing the volume of the container to expel treatment through the one or plurality of nozzles.

9. The cartridge of claim 8 additionally comprising an actuator and pin, the actuator moving the pin to break the vacuum.

10. The cartridge of claim 7 wherein the means to apply increased or reduced pressure comprises a gas connection to the chamber.

11. The cartridge of claim 10 wherein the gas connection is attached to the outlet of a pump to pressurise the chamber.

12. The cartridge of claim 10 wherein the gas connection is to a container of gas under pressure and in which release of the gas from the container of gas into the chamber deforms the container forcing treatment through the one or plurality of nozzles.

13. The cartridge of claim 1 in which the one or plurality of nozzles are pressure sensitive and open only if the treatment pressure is within the correct pressure range.

14. The cartridge of claim 6 which is circular and additionally comprising an induction motor to impart rotation to the cartridge.

15. The cartridge of claim 1 having an internal container which has a plunger connected by tubes to the one or plurality of nozzles, wherein the means to apply increased or reduced pressure to the container, comprises depression of the plunger to expel treatment from the container through the tubes to the one or plurality of nozzles, the plunger being depressed by an actuator arm connected to the plunger to release treatment from the container.

16. The cartridge of claim 15 mounted on a base and wherein the plunger engages against the actuator arm extending from the base into the cartridge, movement of the actuator arm being controlled by an actuator in the base.

17. The cartridge of claim 1 in which the internal container containing treatment has an outlet connected to a servo motor, wherein the means to apply increased or reduced pressure to the container comprises the servo motor being connected through one or more tubes to one or more nozzles to pump treatment in the container to the nozzles.

18. The cartridge of claim 17 having the internal container having an outlet connected to a plurality of servo motors, each servo motor being connected through a tube to a nozzle to pump treatment in the container to the nozzle.

\* \* \* \* \*